United States Patent [19]

Taracatac et al.

[11] Patent Number: 4,495,177

[45] Date of Patent: Jan. 22, 1985

[54] GEL TABLETING AGENT

[75] Inventors: Corazon A. Taracatac, Hayward; Luis Flores, Castro Valley; Viren Chaudhry, Fremont, all of Calif.

[73] Assignee: Shaklee Corporation, San Francisco, Calif.

[21] Appl. No.: 458,627

[22] Filed: Jan. 17, 1983

[51] Int. Cl.³ ............... A61K 9/26; A61K 33/26; A61K 31/375

[52] U.S. Cl. .................. 424/147; 424/140; 424/144; 424/145; 424/154; 514/960; 514/474

[58] Field of Search ......... 424/145, 280, 361, 140, 424/144, 145, 147, 154, 280

[56] References Cited

U.S. PATENT DOCUMENTS

| | | | |
|---|---|---|---|
| 3,293,132 | 12/1966 | Stoyle et al. | 424/280 |
| 3,446,894 | 5/1969 | Magid | 424/280 |
| 3,446,899 | 5/1969 | Cavalli et al. | 424/280 |
| 3,453,368 | 7/1969 | Magid | 424/280 |
| 3,459,863 | 8/1969 | Apelian et al. | 424/280 |
| 3,490,742 | 1/1970 | Nichols et al. | 424/280 |
| 3,493,659 | 2/1970 | Magid | 424/280 |
| 3,622,677 | 11/1971 | Short et al. | 424/280 |
| 3,627,583 | 12/1971 | Troy et al. | 424/280 |
| 3,639,168 | 2/1972 | Monti et al. | 424/280 |
| 3,639,169 | 2/1972 | Broeg et al. | 424/280 |
| 3,642,535 | 2/1972 | Graham et al. | 424/280 |
| 3,857,939 | 12/1974 | Green et al. | 424/280 |
| 3,873,694 | 3/1975 | Kanig | 424/280 |
| 4,013,775 | 3/1977 | Nelson et al. | 424/361 |
| 4,036,948 | 7/1977 | Kitamori et al. | 424/280 |
| 4,066,829 | 1/1978 | Nair et al. | 424/180 |
| 4,070,488 | 1/1978 | Davis | 424/280 |
| 4,203,997 | 5/1980 | Kuppers et al. | 424/280 |
| 4,268,529 | 5/1981 | Davis | 424/280 |
| 4,384,005 | 5/1983 | McSweeney | 426/250 |

FOREIGN PATENT DOCUMENTS

| | | | |
|---|---|---|---|
| 49143 | 4/1982 | European Pat. Off. | 424/280 |
| 2706660 | 8/1978 | Fed. Rep. of Germany | 424/280 |
| 2810141 | 9/1978 | Fed. Rep. of Germany | 424/280 |
| 54-73117 | 6/1979 | Japan | 424/280 |

Primary Examiner—Shep K. Rose
Attorney, Agent, or Firm—Blakely, Sokoloff, Taylor & Zafman

[57] ABSTRACT

A direct compression tableting agent composition is disclosed. In a pharmacologically active tablet containing a mineral and another component reactive with each other, the mineral is mixed with the invented carrier to form a matrix consisting of a compressible granulation. The other reactive component, such as ascorbic acid, is then compressed directly with the granulation into a tablet with improved stability characteristics.

8 Claims, No Drawings

GEL TABLETING AGENT

BACKGROUND OF THE INVENTION

1. Field of the Invention

This invention relates to a composition for use as a direct compression tableting agent for a tablet containing interractive ingredients and the process for making the same. More particularly, this invention relates to a compressible coated iron composition which minimizes interaction with other active ingredients in the tablet. It is specifically suited for use in tablets containing vitamin C to minimize reaction between iron and vitamin C in the tablet formulations.

2. Description of the Prior Art

As a solid dosage form, the tablet is the most popular and useful form of oral medication for dispensing active ingredients such as pharmaceuticals, vitamins, and minerals. The compressed tablet offers several advantages over other solid dosage forms. These advantages include greater accuracy of dosage, more convenient administration, increased durability and stability during storage, shorter production time, and economy and efficiency in storage, packaging and shipping.

Tablets can be prepared using several established methods such as wet granulation, dry granulation, and direct compression. The most desirable method from the standpoint of the processing procedures, equipment and materials is the direct compression method. This method increases the efficiency of tableting operations and reduces costs by requiring the least amount of space and labor.

In a dry direct compression method, the ingredients are simply dry-mixed and then compressed. There is no granulation stage. It is essential that each component is uniformly dispersed within the mixture. Any tendency for component segregation must be minimized to assure that each tablet contains an accurate reproducible dosage. In addition, the mixture must have certain flow characteristics to allow accurate and convenient transport and must be cohesive when compressed. To reduce segregation tendencies the particle size distribution, shape, and density of all the ingredients should be similar. There are only a few substances available in forms which could be compressed directly without further treatment. If these ingredient characteristics are not present, then one of the granulation methods should probably be used.

There are also some limitations to the use of direct compression tableting. First, while compression of some components may produce tablets that do not disintegrate, other components of the tablet may interfere with the compressibility of the tablet composition and thus minimize the usefulness of this method. Second, most materials possess relatively weak intermolecular attraction thereby affecting the compacting of the ingredients into tablets. Third, with some formulations, the percentage of active ingredient is so small that direct compression would be impractical and uneconomical. However, in this case, an inert compressible diluent can be used to increase bulk in order to make the tablet a practical size for compression.

The direct compression method is a rather simple procedure compared to the more complicated and time consuming wet process method. Relatively inexpensive and unreactive chemicals are commonly used as the major component in direct compressible formulations. However, only a very limited number of materials possess the necessary cohesive strength and flowability to allow direct compression without requiring granulation. Modification is often required either by treating the material in some manner during the earlier stages of preparation or by adding a binder or excipient material which will surround or coat the active ingredient thereby forming an easily compressible excipient.

A tableting agent was sought which would protect the active ingredient from other tablet ingredients with which it may react and also have the desirable property of good granulation. The two essential characteristics required for such an agent are fluidity, which is necessary for the transport of the material through the hopper into the feed frame, and compressibility which is the property of forming a stable, compact mass when pressure is applied. Other desirable characteristics include rapid disintegration following ingestion, physiological inertness, capacity to bind poorly compressible ingredients and low cost.

Direct compressible diluents currently available as single entities include microcrystalline cellulose, dibasic calcium phosphate, lactose, spray dried lactose, mannitol and sorbitol. There are also blended vehicles containing all essential materials except the active ingredients.

One method of preparing direct compressible blended excipients is with a spray dryer. The process consists of wetting the powders to form granules, then drying the granules in the same equipment. A fluid bed dryer adapted to function as a wet granulator as well as a dryer is used for this purpose. Finely divided powder materials of a preselected formula are loaded into a container with a fine screen bottom. The container is inserted inside the dryer and thereafter a current of warm air blows upward through the screen mixing the powders. A granulating liquid consisting of a mixture of gums is introduced from above through a spray nozzle and is distributed among the powders by the turbulent air stream. Once all the fluid has been added, drying proceeds to the desired end point. The rate of addition of the liquid and the volume and temperature of the air is regulated such that granules form and remain airborne. The granules must be allowed to grow somewhat larger than desired size because during the drying step, these granules tend to abrade each other and become smaller. Milling of the desired product may be performed to breakdown any large particles.

This process produces granules that have suitable flow and blending properties for compression from powders which have poor tableting characteristics. Additionally, the process provides for control over granule particle size, even distribution of the granulating liquid and a means for precise control over the moisture level in the granulation process. Once this vehicle is prepared, other active ingredients may be added and compressed directly into tablets employing conventional techniques and apparatus.

The term "active ingredient" as used herein means any material intended for ingestion having a beneficial or desirable effect on the user.

SUMMARY OF THE INVENTION

A new direct compression tableting composition is described which prevents reaction of incompatible reactive ingredients in a pharmacologically active tablet. The process of tableting using the composition described herein is also described.

More particularly, an invented composition for direct compression tableting agent containing iron or other active minerals such as copper, zinc, aluminum, stannous and manganese is disclosed, said composition being useful in the production of tablets containing vitamin C (ascorbic acid) whereby interaction between the reactive components is prevented so that the tablet and the ingredients therein are stable for a longer period of time. A binder suitable for use in the preparation of the new direct compression tableting composition is also described.

The new direct compression tableting composition as contemplated by this invention generally comprises iron and water insoluble carrier consisting of a mixture of dicalcium phosphate anhydrous, tricalcium phosphate, malto-dextrin (in ratio of about 6.6:1.1:1.0 in the preferred embodiment) and binder aqueous gum solution of Agar-Agar, Acacia and Locust Bean (in ratio of about 1.0:4.0:2.0 in the preferred embodiment). Iron comprises about 10 weight percent of the compressible granulation. A range of 2.5% to 3.5% solids is preferred in preparing the aqueous gum solution.

The inventive composition is preferably formed by the steps comprising fluidizing a quantity of water insoluble carrier with iron, spraying said fluidized carrier with aqueous gum solution to form compressible granules having a particle size ranging from about 50 microns to about 400 microns in diameter, preferably in the range of 100 microns to about 200 microns, and drying compressible granules to a moisture content of not greater than about 2 wt. percent. A fluidized bed granulation system is used for the fluidizing and spraying steps of granulation. The resulting granulation may then be combined with one or more active ingredients, disintegrating agents, lubricants, and the resulting dry mixture subjected to direct compression to form a tablet. The inventive composition and the preferred process of manufacture will now be more fully described.

DETAILED DESCRIPTION OF THE INVENTION

The compressible granule of the invented composition consists of an iron matrix. The component iron is generally commercially available in a form which is adequately bioavailable such as an iron supplement for human consumption. In the preferred embodiment, an iron salt, ferrous fumarate is used, which contains a minimum of 31.3% of total iron of which not more than 2% is in the ferric state when used as a special dietary and nutritional supplement.

Absorption of the mineral iron is enhanced when combined with ascorbic acid. However, incompatibility exists when both ingredients are present in the formulation. The use of the iron matrix in the invented composition can mitigate this problem. A stable formula was prepared wherein ferrous fumarate, a fine dense powder, is coated with a mixture of substantially water insoluble carriers.

Materials suitable as carriers in the present invention are inert, substantially water insoluble particulate solids, preferably of a particle size of about 3 to 20 microns. Particularly preferred carriers include dicalcium phosphate anhydrous, tricalcium phosphate, malto-dextrin and mixtures thereof. These edible substantially water insoluble inorganic salts and hydrolyzed carbohydrates are commercially available in particulate or powdered form, but lack sufficient compressibility for use as direct compression tableting excipients. In tableting formulations of the prior art, these substances have functioned as bulking agents, glidants, diluents, and the like. As a mixture, the concentration of the above excipient components may be in the range of 34% to 76% dicalcium phosphate anhydrous, 11%–23% tricalcium phosphate, and 11% to 28% malto-dextrin by weight.

The carrier used to produce the compressible granule of the inventive composition comprises a combination of dicalcium phosphate anhydrous, tricalcium phosphate, and malto-dextrin in ratio by of about 6.6:1.1:1.0. A natural edible colorant such as beet powder may also be incorporated at this stage to provide a tablet with a distinctive aesthetic appearance.

Since iron and the carrier lack sufficient cohesion to form a suitable hard tablet, a binder solution is incorporated into the formation to produce a compressible granulation. Suitable materials useful as binders for the invented composition include natural gum products such as Agar-Agar, Acacia, Locust Bean, Tragacanth, Gelatin, and Gum Ghatti. These animal and plant hydrocolloids may be used as dry powder or dissolved or slurried in a liquid. They impart a cohesiveness to the tablet formulation which insures that the tablet remain intact after compression, as well as improve the free flowing qualities by forming granules of predetermined hardness and size.

In the preferred embodiment, the binders, 0% to 15% Agar-Agar, 55% to 70% Acacia, and 20% to 30% Locust Bean Gum are combined in a compatible combination to increase the binding capacity or adhesiveness of the carrier. A ratio of about 1.0:4.0:2.0 of the gums dispersed in hot water, minimum 75 degrees Centigrade, produces a strong binding solution suitable for the formation of the compressible granule in the preferred embodiment of the invented composition.

The following specific example further illustrates the present invention and is not, as such, a limitation thereon. Various modifications and changes may be made without departing from the spirit and scope of the present invention.

Other minerals may be used with the present invention in place of the iron, such as copper, aluminum, stannous, zinc and manganese. Each of these minerals are active pharmacological agents, which may to some extent, react with ascorbic acid, and thereby destabilize a tablet comprising both a mineral from the above group and ascorbic acid.

Preparation of the invented composition wherein the compressible granule is formed from ferrous fumarate and a suitable combination of substantially water insoluble carriers for iron is exemplified in the following Example.

EXAMPLE

A Glatt Granulator WSG-15 was charged with 1.5 kg. ferrous fumarate, 10 kg. dicalcium phosphate anhydrous, 1.7 kg. tricalcium phosphate, 1.6 kg. malto dextrin, and 0.3 kg. beet powder. The spray nozzle equipped with a 1.8 mm liquid orifice was positioned at the height of #5 setting. Meanwhile, 14 g. of agar-agar, 56 g. acacia, and 28 g. locust bean gum was dispersed in 4.0 liters of hot water, minimum 75 degrees C., in a separate container to form a viscous gum solution.

The granulator powder contents were fluidized in an air stream. When the outlet air temperature reached 35 degrees C., spraying of the gum solution commenced, by means of a pulsating pump. Fluidization was maintained during the spray cycle by adjusting the outlet air flaps from an initial setting of 30% to a 45% opening. The outlet air temperature during the spray cycle was maintained between 30 degrees C. and 38 degrees C.

When all the gum solution was sprayed, the drying cycle started, during which the inlet air temperature was adjusted to between 60 degrees C. and 90 degrees C. to maintain an outlet air temperature between 40 degrees C. to 45 degrees C. for a duration of 15 minutes. After completion of the drying cycle, the granules were discharged into a polyethylene bag. The granulation was screened through a #16 mesh U.S. standard screen. The resultant granule had a moisture content of about 2.0 Wt. %. The process parameters of the modified fluid bed drier are summarized in Table I.

TABLE I

| | |
|---|---|
| Air Dome Setting | Three complete turns down. |
| Inlet Air Temperature | 65 degrees C. |
| Atomization Air | 2½ bars |
| Spray Rate | 200 ml/min. |
| Inlet Air Flap | 100% opening |
| Outlet Air Flap | Adjusted accordingly to maintain a proper level of fluidization during the granulation process, exceeding a 50% opening. |
| Drying Temperature | (outlet) 45 degrees C. held for 15 minutes (inlet 60 degrees C. - 90 degrees C. |
| Shake Time | Approximately twice/minute for a duration of 3–5 sec. |

A typical formulation using the prepared iron matrix granulation (T-120) is shown in Table II.

TABLE II
PREPARATION OF IRON C TABLET

| Ingredients | Quantity in Milligrams per Tablet T-120 |
|---|---|
| Iron Matrix Granulation | 493.0 |
| Ascorbic Acid | 81.0 |
| Modified Cellulose Gum | 12.0 |
| Barley Flour | 1.0 |
| Spinach powder | 1.0 |
| Silica Gel | 3.0 |
| Partially hydrogenated vegetable Oil, free flowing powder | 3.0 |
| Calcium Stearate | 6.0 |

The iron matrix granulation was blended with the rest of the ingredients in a PK Blender and compressed on a Stokes D3 rotary tablet machine using 7/16 inch diameter deep concave punches at 500 TPM.

For comparative purposes, other formulations prepared by a dry direct compression method wherein the ingredients are simply dry-mixed and then compressed, are contained in Table III and the tablets are identified as Formula T-37.

TABLE III
Tablet Formula Variations
Quantity in Milligrams per Tablet

| Ingredients | T-37 | T-63 | T-93 | T-20 | T-35 | T-41 | T-19 |
|---|---|---|---|---|---|---|---|
| Dicalcium Phosphate Dihydrate, Unmilled | 458.1 | 459.8 | 359.1 | | | | |
| Mannitol Granular | | | | 427.0 | | | |
| Corn Syrup Solids | | | | | 427.0 | | |
| Dextrose Anhydrous | | | | | | 427.0 | |
| Sorbitol | | | | | | | 427.0 |
| Ascorbic Acid | 105.9 | | 70.7 | 74.0 | 74.0 | 74.0 | 74.0 |
| Ferrous Fumarate | | 104.2 | 60.4 | 61.0 | 61.0 | 61.0 | 61.0 |
| Modified Cellulose Gum | 24.0 | 24.0 | 3.0 | 24.0 | 24.0 | 24.0 | 24.0 |
| Soy Fiber | | | 42.0 | | | | |
| Carnuba Wax | | | 42.0 | | | | |
| Beet Powder | | | 6.0 | | | | |
| Barley Flour | | | 3.0 | 1.0 | 1.0 | 1.0 | 1.0 |
| Spinach powder | | | 1.8 | 1.0 | 1.0 | 1.0 | 1.0 |
| Calcium Stearate | 3.0 | 3.0 | 3.0 | 6.0 | 6.0 | 6.0 | 6.0 |
| Partially Hydrogenated Vegetable Oil, Free Flowing Powder | 6.0 | 6.0 | 6.0 | 3.0 | 3.0 | 3.0 | 3.0 |
| TABLET WEIGHT | 600.0 | 600.0 | 600.0 | 600.0 | 600.0 | 600.0 | 600.0 |

All formulations were blended in a PK Blender and compressed on Stokes D3 rotary tablet machine using 7/16 inch diameter deep concave punches at 500 TPM.

There is a natural tendency for products containing iron and ascorbic acid combination to discolor during storage under normal conditions of temperature and humidity. The presence of the metal iron increases the rate of oxidation of the ascorbic acid thus causing decomposition.

Detection of the incompatibility of tablet components early in the development of a particular tablet make it possible to formulate a product with ingredients that are least likely to interact.

In order to determine the stability characteristics of the formulations from Table II and Table III, tablets were subjected to accelerated aging tests at elevated temperatures and relative humidities (RH). Tablets were stored in 100 cc amber glass bottles with uniformly torqued screw cap closures at various conditions—i.e., 45 degrees C./75% RH and 55 degrees C./75% RH for a period of four weeks. Color stability was ascertained rapidly by visual examination of tablets for color change.

Table IV summarizes the physical characteristic of the various tablet formulations after four weeks exposure at 45 degrees C./75% RH and 55 degrees C./75% RH.

TABLE IV
Physical Profile of Iron plus C Tablet Formulations

| | Appearance* | |
|---|---|---|
| Formula | 45 Degrees C/75% RH | 55 Degrees C/75% RH |
| T-37 | 4 | 5 |
| T-63 | 2 | 3 |
| T-93 | 4 | 5 |
| T-20 | 3 | 4 |
| T-35 | 4 | 5 |
| T-41 | 3 | 4 |
| T-19 | 4 | 5 |
| T-102 | 1 | 1 |

*Appearance graded on a 1 to 6 scale with the initial appearance as 1.

No color change was observed on tablets prepared from the formulation containing the inventive iron matrix granulation (T-120) at any storage conditions after four weeks. However, tablets produced from Table III formulations showed various degrees of color degradation at all conditions studied.

Table V further exemplifies the physical and chemical analyses comparison between two of the formulations, T-120 and T-93.

TABLE V

Physical and Chemical profile of Iron plus C Tablet

| Formula | Storage Condition | No. of weeks | Appearance* | Mg. Ascorbic Acid/Tablet | Relative % Loss |
|---|---|---|---|---|---|
| T-120 | Initial | 0 | 1 | 75.6 | — |
| | 45° C./75% RH | 4 | 1 | 74.8 | 1.1 |
| | 55° C./75% RH | 4 | 1 | 73.5 | 2.8 |
| T-93 | Initial | 0 | 1 | 73.4 | — |
| | 45° C./75% RH | 4 | 4 | 54.7 | 25 |
| | 55° C./75% RH | 4 | 5 | 42.6 | 42 |

*Appearance graded on a 1 to 6 scale with the initial appearance as 1.

Ascorbic acid concentrations were determined by the U.S.P XX Method. The Label Claim is 60 mg per tablet.

Results from Table V show that formula T-120 containing the inventive iron matrix granulation produced a very stable product. No apparent color change and no considerable loss in ascorbic acid was observed. Color stability was found to be closely related to chemical stability.

Theoretically, assuming that for every ten degree change in temperature the reaction rate doubles, at ambient temperature (25 degrees C./75% RH) the relative percentage loss after four weeks would be 0.3% for Formula T-120 and 6.3% for Formula T-93. If the proposed expiration data of the formulation is two years, the apparent percentage loss in potency would be 7.8% for Formula T-120 and a total 100% loss for Formula T-93. In general, a 10% loss in potency from label claim is acceptable as the maximum allowable change in potency during the shelf life or effective life of a product.

Table VI provides a chemical profile of an iron plus Vitamin C tablet formulation based on the T-120 formula containing the inventive iron matrix granulation. Tablets were produced on a full-scale production equipment. Stability characteristics of the tablets stored in polystyrene containers without dessicant were assessed at 0 degrees, 25 degrees C./75% RH, 35 degrees C./75% RH, 45 degrees C./75% RH, and 55 degrees C./75% RH over a period of sixteen weeks. The tablets were stored in a 100 cc polystyrene container. Potency was determined at various intervals.

TABLE VI

Chemical Profile of Iron Tablet + Vitamin C
Label Claim: Vit. C = 60.0 mg/tablet
Milligrams Vitamin C per Tablet

| Storage Condition | Zero Time | 4th week | 8th week | 12th week | 16th week |
|---|---|---|---|---|---|
| 0° C. | 74.5 | 76.2 | 76.2 | 73.9 | 73.9 |
| 25° C./75% RH | | 76.5 | 76.0 | 74.4 | 74.8 |
| 35° C./75% RH | | 75.6 | 75.5 | 73.6 | 71.7 |
| 45° C./75% RH | | 75.9 | 70.0 | 63.9 | |
| 55° C./75% RH | | 65.5 | 49.7 | 21.8 | |

To confirm and expand the conclusions reached in previous studies concerning the stability of the formulations, more stability data from a full-scale production were collected. It was determined that the data follows an Arrhenius relationship. An energy of activation was calculated and used to estimate the stability of the formulation over a different range of temperatures. Regression analysis was performed to estimate the crude shelf life of the formulation. The time it would take for important properties to reach product specification limits may be estimated from the regression lines. Table VII sets forth the calculations for the estimated shelf life of the product.

TABLE VII

Chemical Stability Prediction
Label Claim: Vit. C = 60.0 mg/tablet

| t °C. | T °K. | 1/T | K mg AA/week | log K | shelf life years |
|---|---|---|---|---|---|
| 35 | 308 | 0.003247 | 0.34 | −0.4685 | |
| 45 | 318 | 0.003145 | 1.22 | 0.0864 | |
| 55 | 328 | 0.003049 | 4.83 | 0.6839 | |
| 25 | 298 | 0.003356 | 0.076739* | −1.115042* | 4.5 years* |

*Calculated from regression line.
AA = Ascorbic Acid
(1) Expiration date to be at 90% label claim:

$$t_{90} = \frac{(72 - 54)}{0.076729} \times 1/52 = 4.5 \text{ yrs},$$

(2) If 2 years is desired then:
Loss after 2 years = (0.076729) (104) = 7.98 mg ≈ 8.0 mg AA Based on physical and chemical stability studies, formulation containing the inventive iron matrix granulation produced a very stable product. Visual examination of the tablets showed no apparent color change and no significant loss in potency at ambient temperature (25 degrees C./75% RH) after sixteen weeks.

To visualize the structure of the inventive iron matrix granulation, scanning electron microscope (SEM) was employed. Comparison of the fine individual spherical dense particles of ferrous fumarate with the inventive iron matrix composition demonstrates that the invented composition does not consist of individual crystals, but of aggregates of microcrystals glued together. These aggregates are free flowing and under the stress of compaction, each particle deforms along many planes, which makes this material compressible.

Therefore we claim:

1. A composition for a direct compression tableting agent comprising:
   a pharmacologically active mineral selected from the group consisting of iron, copper, aluminum, stannous, zinc and manganese;
   a binder solution comprising at least one gum product selected from the group consisting of Agar-Agar, Locust Bean, Tagacanth, gelatin and gum ghatti; and
   a substantially water insoluble compressible carrier comprising a mixture of about: 34% to 75% dicalcium phosphate anhydrous, 11% to 23% tricalcium phosphate, and 11% to 28% maltodextrin, said mineral and carrier being granulated together with said binder solution to form a mineral matrix granulation; and
   ascorbic acid blended with said mineral matrix granulation provided in a pharmacologically beneficial amount;
   whereby said mineral matrix granulation prevents substantial physical interaction between said mineral and said ascorbic acid such that reaction therebetween is minimized.

2. The composition according to claim 1 wherein said mineral is a bioavailable iron supplement comprising ferrous fumarate containing at least 31.3% total iron of which not more than 2% is in the ferric state.

3. The composition according to claim 1 wherein said carrier comprising a mixture of dicalcium phosphate anhydrous, tricalcium phosphate and malto-dextrin in a ratio of about 6.6:1.1:1.0.

4. The composition according to claim 1 wherein said binder solution comprises about 0% to 15% Agar-Agar, 55% to 70% Acacia and 20% to 30% Locust Bean Gum.

5. The composition according to claim 4 wherein said binding solution comprises Agar-Agar, Acacia and Locust Bean Gum in a ratio of about 1.0:4.0:2.0 dispersed in an aqueous solution at a temperature of at least 75 degrees Centrigrade.

6. The composition according to claim 1 wherein said composition comprises a compressible granulation having a particle size in the range of about 100 microns to 200 microns.

7. A composition for an improved compression tableting agent wherein the improvement is the prevention of substantial reaction between ascorbic acid and iron in a tablet, comprising approximately by weight:
(a) five parts iron matrix granulation comprising:
  (i) 1.5 parts ferrous fumarate,
  (ii) 13.3 parts water insoluble carrier comprising dicalcium phosphate anhydrous, tricalcium phosphate and maltodextrin in a weight ratio of about 6.6:1.1:1.0, and,
  (iii) 4 parts binding agent comprising Agar-Agar, Acacia and Locust Bean Gum in a ratio of about 1.0:4.0:2.0 dispersed in water at a temperature of at least 75 degrees Centrigrade; and
(b) one part ascorbic acid, whereby said composition is compressible into a tablet.

8. A composition for an improved compression tableting agent comprising approximately by weight:
(a) 493 parts iron matrix granulation comprising:
  (i) 1.5 parts ferrous fumarate,
  (ii) 10.0 parts dicalcium phosphate, anhydrous
  (iii) 1.7 parts tricalcium phosphate
  (iv) 1.6 parts malto-dextrin, (v) 0.3 parts beet powder, and
  (vi) 4.0 parts binding solution comprising by weight:
  (vii) 4.0 parts water at a temperature of at least 75 degrees C,
  (viii) 0.014 parts Agar-Agar,
  (ix) 0.056 parts Acacia, and
  (x) 0.028 parts Locust Bean Gum;
(b) 81.0 parts ascorbic acid
(c) 12.0 parts modified cellulose gum,
(d) 1.0 parts barley flour,
(e) 1.0 parts spinach powder,
(f) 3.0 parts silica gel,
(g) 3.0 parts partially hydrogenerated vegetable oil, and
(h) 6.0 parts calcium stearate.

* * * * *